United States Patent
Cho et al.

(10) Patent No.: US 8,705,039 B2
(45) Date of Patent: Apr. 22, 2014

(54) SURFACE PLASMON RESONANCE SENSOR USING VERTICAL ILLUMINATING FOCUSED-BEAM ELLIPSOMETER

(75) Inventors: Hyun Mo Cho, Daejeon (KR); Yong Jai Cho, Daejeon (KR); Won Chegal, Daejeon (KR)

(73) Assignee: Korea Research Institute of Standards and Science (KR)

( * ) Notice: Subject to any disclaimer, the term of this patent is extended or adjusted under 35 U.S.C. 154(b) by 272 days.

(21) Appl. No.: 13/121,079

(22) PCT Filed: Nov. 30, 2009

(86) PCT No.: PCT/KR2009/007084
§ 371 (c)(1),
(2), (4) Date: Apr. 18, 2011

(87) PCT Pub. No.: WO2010/062150
PCT Pub. Date: Jun. 3, 2010

(65) Prior Publication Data
US 2012/0057146 A1    Mar. 8, 2012

(30) Foreign Application Priority Data
Nov. 28, 2008  (KR) .......................... 10-2008-0119912

(51) Int. Cl.
*G01N 21/55* (2006.01)
(52) U.S. Cl.
USPC .......................................... 356/445; 356/369
(58) Field of Classification Search
USPC ........................................ 356/364–370, 445
See application file for complete search history.

(56) References Cited

U.S. PATENT DOCUMENTS

| | | | |
|---|---|---|---|
| 4,997,278 A * | 3/1991 | Finlan et al. | 356/128 |
| 6,417,925 B1 * | 7/2002 | Naya | 356/445 |
| 2001/0004348 A1 * | 6/2001 | Ueyanagi | 369/118 |
| 2001/0009541 A1 * | 7/2001 | Ueyanagi | 369/112.23 |
| 2004/0125460 A1 * | 7/2004 | Lee et al. | 359/664 |
| 2006/0221343 A1 | 10/2006 | Bouhelier et al. | |
| 2008/0032326 A1 | 2/2008 | Greenbaum et al. | |
| 2010/0045985 A1 | 2/2010 | Lee et al. | |

FOREIGN PATENT DOCUMENTS

| | | |
|---|---|---|
| KR | 10-2007-0039335 | 4/2007 |
| KR | 10-0742982 | 7/2007 |

OTHER PUBLICATIONS

International Search Report—PCT/KR2009/007084 dated Jul. 26, 2010.

* cited by examiner

*Primary Examiner* — Tarifur Chowdhury
*Assistant Examiner* — Michael P Lapage
(74) *Attorney, Agent, or Firm* — Cantor Colburn LLP

(57) ABSTRACT

Provided is a multi-channel surface plasmon resonance sensor using beam profile ellipsometry; and, more particularly, to a high sensitive measuring technology, which is coupled with a vertical illumination type focused-beam ellipsometer using a multi-incident angle measurement method, and a surface plasmon resonance (SPR) sensing part deposited with a metal thin film. The multi-channel surface plasmon resonance sensor includes a vertical illumination type focused-beam ellipsometer, in which light is polarized; a surface plasmon resonance (SPR) sensing part which is provided at the objective lens part of the focused-beam ellipsometer so as to generate SPR according to an angle change of the polarized light; and a flow unit which supplies a buffer solution containing a bio material binding to or dissociation from the metal thin film generating surface plasmon, wherein the SPR and the ellipsometric phase change by change in an angle and a wavelength are simultaneously detected.

10 Claims, 5 Drawing Sheets

SURFACE PLASMON RESONANCE SENSOR USING VERTICAL ILLUMINATING FOCUSED-BEAM ELLIPSOMETER

TECHNICAL FIELD

The present invention claims priority of Korean Patent Application No. 10-2008-0119912, filed on Nov. 28, 2008, which is incorporated herein by reference.

The present invention relates to a surface plasmon resonance (SPR) sensor using beam profile ellipsometry, which can simultaneously detect ellipsometric phase change and SPR by using a metal thin film generating the SPR and a vertical illumination type focused-beam ellipsometer using a multi-incident surface/multi-incident angle measurement method; and, more particularly, to a high sensitive measuring technology, which is coupled with a polarizer, an ellipsometer using an analyzer, a SPR sensing part (or a high numerical aperture objective lens, a refractive index matching material, a glass substrate deposited with a metal thin film) so as to allow real-time SPR measurement.

BACKGROUND ART

In general, an ellipsometer is a measuring device which obtains optical properties of a sample by measuring a change in a polarizing state after light having a specific polarizing state is incident to a surface of the sample and reflected from it, and then analyzing the measured values. Particularly, in the semiconductor industrial field using various manufacturing methods of nano thin film, the ellipsometer is widely used as a non-destructive and non-contacted real-time measuring technology for estimating physical properties of the manufactured nano thin films. Typically, the ellipsometer obtains data about an angle change relevant to the amplitude of light reflected from the sample.

A conventional ellipsometer can be applied to a semiconductor sample, but can not be applied to a biomaterial like protein. Preferably, a surface plasmon resonance (SPR) sensor is used for measure the properties of the biomaterial.

Electrons on a surface of a metal are collectively vibrated by normal directional vibration with respect to the surface of the metal, and this motion is called 'surface plasmon wave'. The vibration of quantized electrons is the surface plasmon. In order to quantitatively analyze a material using a phenomenon that the surface plasmon is excited by light waves, there have been proposed various SPR sensors.

The resonance phenomenon of the surface plasmon is applied to a polarizer, or mainly applied to a bio-sensor, i.e., an opto-chemical sensor by using sensitivity with respect to polarizing characteristic of light.

A sensor using a resonance absorbing effect of the surface plasmon, i.e., a surface plasmon sensor is used for measuring a change in a concentration, a thickness or a refractive index of a dielectric substance contacted with the surface of the metal, and also may be used as a bio-sensor for measuring a change in a concentration of a sample like a bio material in real time without labeling.

FIG. 1 shows an example of a conventional SPR sensor.

As shown in the drawing, the SPR sensor includes a light source 110, a polarizer 120 for polarizing light emitted from the light source 110, a prism 130 in which the polarized light is incident and then reflected, a glass substrate 140 which is provided on one surface of the prism 130 and to which the polarized light passing through the prism 130 is incident, a metal thin film 150 which is coated on the glass substrate 140 with a few tens nanometer-sized thickness so that the polarized light passing through the glass substrate 140 is reflected by surface plasmon resonance, and a light receiving part 160 for detecting the light reflected by the metal thin film and passed through the glass substrate 140 and the prism 130. Meanwhile, the metal thin film is contacted with a sample 170. If the concentration, thickness or refractive index of the sample 170 is changed between the metal thin film 150 and the sample 170, conditions of the SPR are correspondingly changed. Thus, the quantity of light reflected to the light receiving part 160 is changed, and the change in the concentration of the sample 170 contacted with the metal thin film 150 is measured by using this phenomenon.

A conventional SPR sensor only using reflexibility measures an intensity of light or a change in angle which designates the minimal reflexibility. But a surface plasmon resonance (SPR) sensor using ellipsometry can obtain phase information as well as amplitude of light corresponding to reflexibility information. Particularly, since an ellipsometric phase change is sensitive under an optimal SPR condition, it is possible to obtain high sensitive measurement precision.

Especially, when a low molecular material used as a new drug candidate is conjugated to target protein, it is required to provide the extremely sensitive measurement precision. In the optimal SPR condition, it is possible to improve the measurement precision by measuring the ellipsometric phase change.

DISCLOSURE OF INVENTION

Solution to Problem

An embodiment of the present invention is directed to providing a SPR sensor using beam profile ellipsometry, which has high sensitive measurement precision by using a phase change that is sensitive under an optimal SPR condition.

To achieve the object of the present invention, the present invention provides a multi-channel surface plasmon resonance sensor using beam profile ellipsometry, including a vertical illumination type focused-beam ellipsometer, in which light is polarized, a part of the polarized light is focused to a metal thin film 42 by using an objective lens part, and then the polarized light reflected from the metal thin film 42 is detected; a surface plasmon resonance (SPR) sensing part 40 which is provided at the objective lens part of the focused-beam ellipsometer so as to generate surface plasmon resonance (SPR) according to an angle change of the polarized light; and a flow unit 1 which supplies a buffer solution containing a bio material binding to or dissociation from the metal thin film generating surface plasmon, wherein the SPR and the ellipsometric phase change by change in an angle and a wavelength are simultaneously detected.

Preferably, the vertical illumination type focused-beam ellipsometer comprises a light source 10; a polarizer 20 for polarizing light emitted from the light source 10; a beam splitter 30 for splitting the light polarized from the polarizer 20; an objective lens part for focusing a part of the polarized light split from the beam splitter 30 to a metal thin film having the multi-channels; an analyzing means 50 for polarizing the light reflected from the metal thin film 42 and passed through the beam splitter 30 and then detecting the polarized light; an optical detector 60 for detecting amplitude and phase of the light detected by the analyzing means; and a processing device 70 for processing the ellipsometric phase change detected by the optical detector 60.

Preferably, the light source 10 is one of a light source for emitting a short wavelength or a wavelength band of an ultraviolet ray, visible ray or an infrared ray, and a wavelength variable light source of a wavelength variable laser or diode.

Preferably, the analyzing means 50 is one of an analyzer, a single polarizing-beam splitter, a beam splitter and a polarizer.

Preferably, the SPR sensing part 40 includes a first lens 41 which is a converging lens for focusing a part of the polarized light; and a second lens 43 which functions as a high aperture objective lens for a microscope together with the first lens 41, and which is formed into a single spherical or aspherical lens or the group of spherical or aspherical lenses so as to have the metal thin film 42 deposited at a lower side thereof.

Preferably, the SPR sensing part 40 includes a third lens 44 which functions to focus a part of the polarized light and which is formed into an integral type high aperture objective lens or solid immersion lens (SIL) having a plurality of lenses; a glass substrate 45 which is provided at a lower side of the third lens 44 so as to have the metal thin film 42 deposited at a lower side thereof; and a refractive index matching material 46 which is interposed between the third lens 44 and the glass substrate 45 so as to match a refractive index of the third lens 44 and a refractive index of the glass substrate 45 with each other.

Preferably, the analyzing means 50 includes a second polarizer 51 for polarizing the light reflected from the metal thin film 42 and passed through the SPR sensing part 40 and the beam splitter 30; a slit 52 for passing the light polarized by the second polarizer 51; and a monochromator 53 for detecting the polarized light passing through slit 52.

Preferably, the multi-channel surface plasmon resonance sensor further includes a means for rotating the polarizer 20 or the second polarizer 51, or polarization-modulating the light.

Preferably, the multi-channel surface plasmon resonance sensor further includes a means for rotating the second polarizer 51 in a vertical direction to a running direction of the light, so that the light polarized by the second polarizer 51 can be independently detected at each incident angle by the monochromator 53.

Preferably, the multi-channel surface plasmon resonance sensor further includes a compensator 80 which is disposed between the beam splitter 30 and the SPR sensing part 40 or between the beam splitter 30 and the optical detector 60 so as to compensate the light split from the beam splitter 30.

Preferably, the multi-channel surface plasmon resonance sensor further includes a means for rotating the compensator 80 in a vertical direction to a running direction of the light, so that the light compensated by the compensator 80 can be detected at each incident angle by the polarized light detecting part 50.

Preferably, the multi-channel surface plasmon resonance sensor further includes a collimator 90 which is disposed between the light source 10 and the polarizer 20 so as to convert the light emitted from the light source 10 into parallel light and then transmit the parallel light to the polarizer 20.

Preferably, the SPR sensing part 40 includes a first lens 41 which is a converging lens for focusing a part of the polarized light; a second lens 43 which is formed into a single spherical or aspherical lens or the group of spherical or aspherical lenses so as to form a high numerical aperture objective lens for a microscope together with the first lens 41; a glass substrate (not shown) which is provided at a lower side of the second lens 43 and of which a lower side is deposited with the metal thin film 42; and a refractive index matching material (not shown) which is interposed between the second lens 43 and the glass substrate so as to match a refractive index of the second lens 43 and a refractive index of the glass substrate with each other.

Preferably, the converging lens 41 is formed into one of a biconvex shape, a planoconvex shape and a meniscus shape.

Advantageous Effects of Invention

According to the present invention, it is possible to measure a conjugation property and a conjugation dynamic property of the bio material in real time by simultaneously measuring the amplitude and the phase of the light and thus simultaneously measuring the ellipsometric phase change and the SPR measurement caused by the angle change and the wavelength change. Further, since it is possible to perform the measurement in the optimal SPR condition in which the phase change is sensitive, it is possible to perform the higher sensitive measurement than the conventional SPR measurement using only the reflexibility.

While the present invention has been described with respect to the specific embodiments, it will be apparent to those skilled in the art that various changes and modifications may be made without departing from the spirit and scope of the invention as defined in the following claims.

DETAILED DESCRIPTION OF MAIN ELEMENTS

Figure 1:
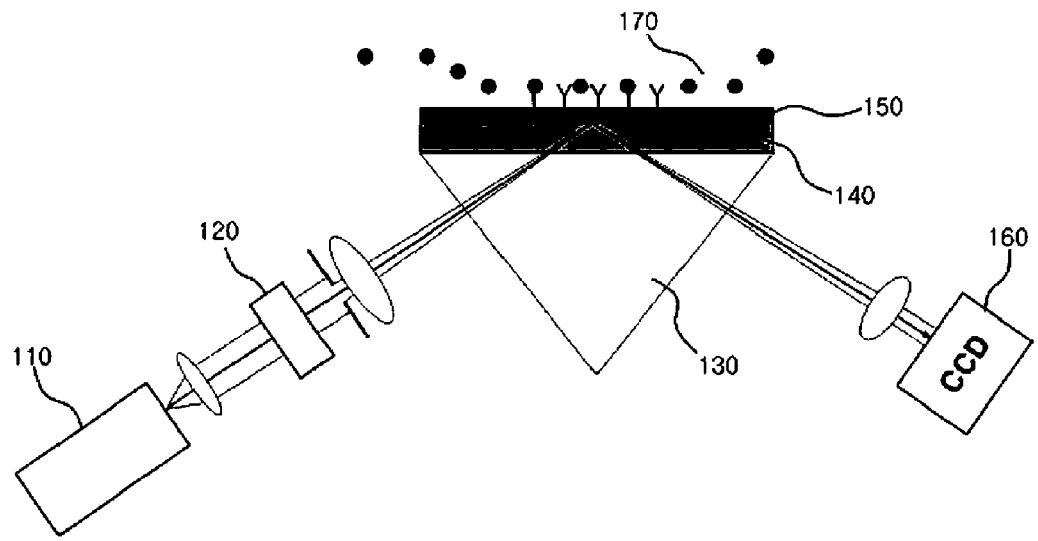
FIG. 1 is a schematic view of a conventional surface plasmon resonance (SPR) sensor.

1: flow unit 1*a*: bio thin film
1*b*: buffer solution 10: light source
20: polarizer 30: beam splitter
40: SPR sensing part 41: first lens
42: metal thin film 43: second lens
44: third lens 45: glass substrate
46: refractive index matching material
50: polarized detecting part
51: second polarizer 52: slit
53: monochromator 60: optical detector
70: processing device 80: compensator
90: collimator

MODE FOR THE INVENTION

The present invention relates to a surface plasmon resonance sensor using beam profile ellipsometry; and, more particularly, to a high sensitive measuring technology, which is coupled with a polarizer, an ellipsometer using an analyzer, a SPR sensing part (or a high numerical aperture objective lens, a refractive index matching material, a glass substrate deposited with a metal thin film) so as to allow real-time SPR measurement. The beam profile ellipsometry can simultaneously measure amplitude and phase of light reflected from a surface of a sample, particularly, if the ellipsometry is performed under optimal surface plasmon resonance (SPR) conditions in which a phase change is sensitive, it is possible to perform the measurement having higher sensitivity than a conventional SPR measuring method only using the reflexibility. A conventional focused beam ellipsometer is used in a semiconductor sample and has no connection with a SPR measurement of the present invention.

Hereinafter, the surface plasmon resonance sensor using beam profile ellipsometry will be described fully with reference to the drawings.

Figure 2:
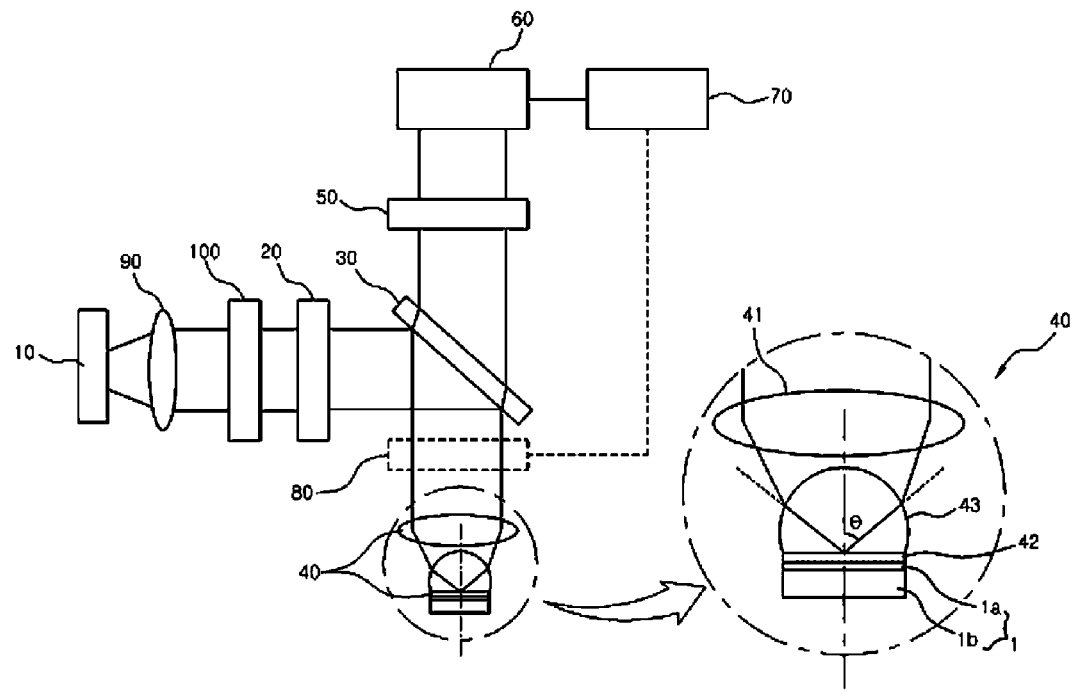
FIG. 2 is a view showing a structure of a SPR sensor using beam profile ellipsometry in accordance with the present invention.
Figure 3:
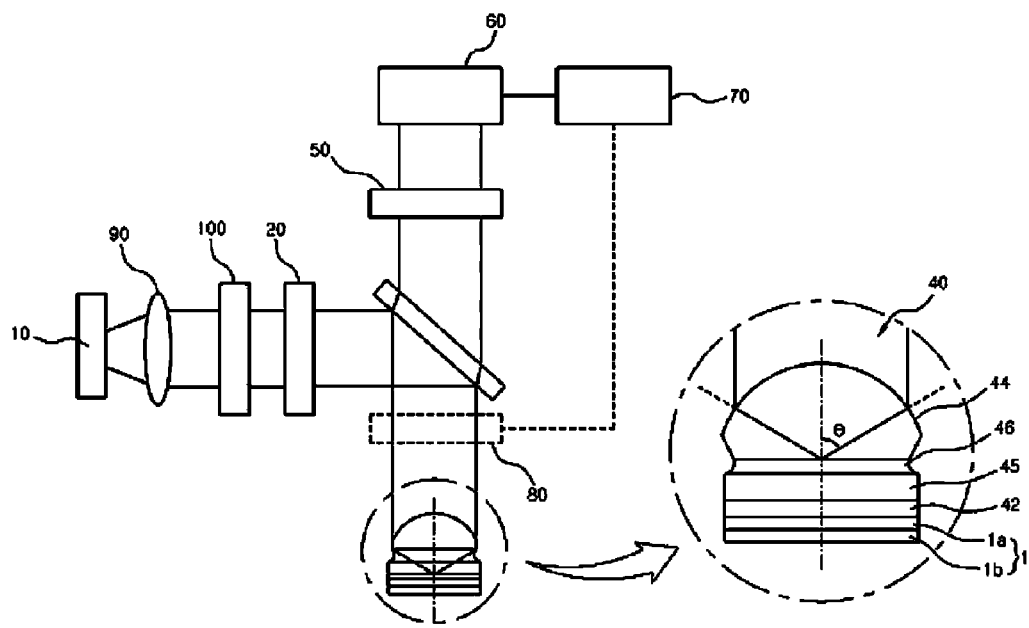
FIG. 3 is a view showing a structure of another type SPR sensor using beam profile ellipsometry in accordance with the present invention.
Figure 4:
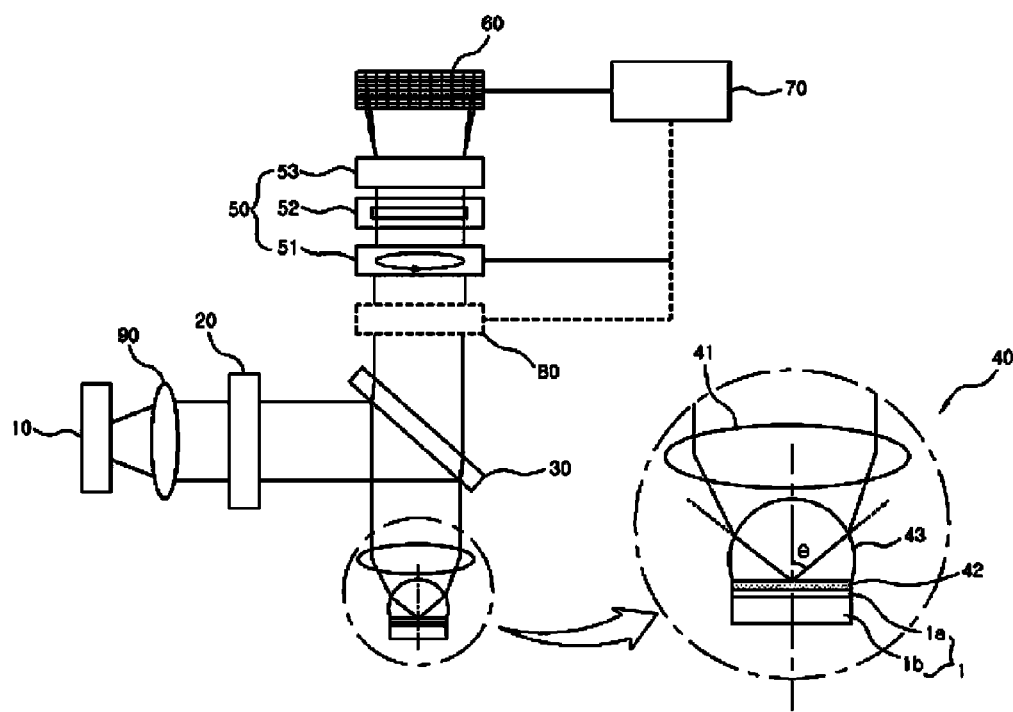
FIG. 4 is a view showing a structure of yet another type SPR sensor using beam profile ellipsometry in accordance with the present invention.

FIG. 2 is a view showing a structure of a SPR sensor using beam profile ellipsometry in accordance with the present invention, FIG. 3 is a view showing a structure of another type SPR sensor using beam profile ellipsometry in accordance with the present invention, and FIG. 4 is a view showing a structure of yet another type SPR sensor using beam profile ellipsometry in accordance with the present invention.

As shown in the drawings, a SPR sensor using beam profile ellipsometry according to the present invention includes a vertical illumination type focused-beam ellipsometer (not shown) having a light source 10, a polarizer 20 for polarizing light emitted from the light source 10, a beam splitter 30 for splitting the polarized light, an objective lens 41, 43 for focusing a part of the split polarized light to a metal thin film 42, a polarized light detecting part 50 for polarizing the light reflected from the metal thin film 42 and detecting the polarized light, an optical detector 60 for detecting amplitude and phase of the polarized light and simultaneously detecting SPR and ellipsometric phase change caused by the angle change and the phase change, and a processing device 70 for processing the detected SPR and ellipsometric phase change; a SPR sensing part 40 including the metal thin film 42 which is coupled with the objective lens 43 of the focused-beam ellipsometer so as to generate the SPR caused by the angle change; and a multi-channel flow unit 1 which supplies a buffer solution including a bio material binding to or dissociation from the metal thin film 42 generating surface plasmon.

As shown in FIGS. 2 and 3, the vertical illumination type focused-beam ellipsometer (not shown) may use a polarizer, a beam splitter and an analyzer, or may use a single polarizing-beam splitter instead of the polarizer, the beam splitter and the analyzer, or may use the beam splitter and the polarizer.

The light source 10 may emit a short wavelength or a wavelength band of an ultraviolet ray, visible ray or an infrared ray. Further, the light source 10 may be a wavelength variable light source of a wavelength variable laser or diode and the like so as to perform the measurement at a desired wavelength proper to the optimal sensitivity condition of the SPR according to a thickness difference of the metal thin film 42.

The polarizer 20 functions to polarize the light emitted from the light source 10.

The beam splitter 30 splits the light polarized from the polarizer 20 and transmits a part of the split light to the SPR sensing part 40.

The objective lens 41, 43 of the SPR sensing part 40 focuses to the metal thin film 42 a part of the polarized light split from the beam splitter 30. At this time, the flow unit 1 for supplying the buffer solution 1b including the bio material provided at a lower side of the metal thin film 42 includes a bio thin film 1a and a micro channel 1c which is formed at a lower side of the bio thin film 1a so as to be filled with the buffer solution 1b.

For example, the SPR sensing part 40 includes two kinds of lenses, i.e., a first lens 41 which is a converging lens for focusing a part of the polarized light split from the beam splitter 30, and a second lens 43 that the metal thin film 42 is deposited on a surface thereof so as to form a high numerical aperture objective lens together with the first lens 41.

The converging lens may be formed into a biconvex shape, a planoconvex shape or a meniscus shape.

After a part of the polarized light split from the beam splitter 30 is focused by the first lens 41, the polarized light focused by the first lens 41 is focused to the metal thin film 42 by the second lens 43. At this time, the second lens 43 is formed into a single spherical or aspherical lens or the group of spherical or aspherical lenses and functions to increase a maximal incident angle of the lens. The second lens 43 may include the metal thin film 42 deposited on a lower flat surface thereof. Alternatively, in a state that the metal thin film 42 is not deposited on the second lens 43, the second lens 43 may include a glass substrate (not shown) which is provided at a lower side of the second lens 43 so as to have the metal thin film 42 deposited at a lower side thereof, and a refractive index matching material (not shown) which is interposed between the second lens 43 and the glass substrate so as to match a refractive index of the second lens 43 and a refractive index of the glass substrate with each other. The metal thin film 42 is formed of a metal material such as Au and Ag and functions to generate the SPR.

As another example (FIG. 3), the SPR sensing part 40 may include an integral lens, the glass substrate and the refractive index matching material. The SPR sensing part 40 includes a third lens 44 which functions to focus a part of the polarized light split from the beam splitter 30 and which is formed into an integral type high aperture objective lens or solid immersion lens (SIL) having a plurality of lenses, the glass substrate 45 which is provided at a lower side of the third lens 44 so as to have the metal thin film 42 deposited at a lower side thereof, and a refractive index matching material 46 which is interposed between the third lens 44 and the glass substrate 45 so as to match a refractive index of the third lens 44 and a refractive index of the glass substrate 45 with each other. Herein, refractive index matching oil and thin film are used as the refractive index matching material 46. Preferably, the glass substrate deposited with the metal thin film 42 has a structure that can be easily replaced with new one. In case that the refractive index matching material 46 is not used, since total reflection is occurred in the air, it is impossible to perform the SPR measurement.

If a part of the polarized light split from the beam splitter 30 is focused by the third lens 44, the focused light is incident to the glass substrate 45 by the refractive index matching material 46, and the incident polarized light is focused to the metal thin film 42 which is deposited at the lower side of the glass substrate 45 and contacted with the flow unit 1 for supplying the buffer solution containing the bio material. If a concentration, a thickness or a refractive index of the bio thin film 1a is changed in the multi-channel flow unit 1, the SPR condition is changed, and the light is reflected and emitted to the glass substrate 45. And the emitted light is passed through the refractive index matching material 46 and then directed to the third lens 44. The light directed to the third lens 44 is passed through the beam splitter 30 and then detected by the polarized light detecting part 50.

The lens used in the present invention includes a high numerical aperture objective lens, a SIL lens and the like.

Herein, the maximal incident angle of the light that is incident to the lens is determined by a numerical aperture NA of the lens and a refractive index n of a medium.

$$\theta_{max} = \sin^{-1}\left(\frac{NA}{n}\right)$$

The polarized lights detecting part 50 functions to polarize the light reflected from the metal thin film 42 and passed through the SPR sensing part 40 and the beam splitter 30 and then detect the polarized light.

Preferably, the polarized light detecting part 50 includes a second polarizer 51 for polarizing the light reflected from the metal thin film 42 and passed through the SPR sensing part 40 and the beam splitter 30, a slit 52 for passing the light polarized by the second polarizer 51, and a monochromator 53 for detecting the polarized light passing through slit 52.

The optical detector 60 functions to detect the amplitude and the phase of the polarized light detected by the analyzer 50.

The processing device 70 processes the SPR and the ellipsometric phase change detected by the optical detector 60.

The processing method in the SPR sensor of FIGS. 2 and 3 is a multi-incident surface/multi-incident angle measurement method, as described below.

A signal corresponding to a unit device (a unit pixel in case of CCD) of the optical detector 60 is read along a path that a diameter is within a desired distance from a center of a signal intensity, and then processed so as to obtain an ellipsometric coefficient (referring to Korean Patent Application No. 10-2007-0115398).

The signal intensity is

I]I$_o$[1+α$_2$ cos 2φ+α$_4$ cos 4φ], and the ellipsometric coefficient ψ, Δ is calculated using a coefficient

α$_2$,
α$_4$.

The ellipsometric coefficient ψ relevant to the amplitude is used for calculating the angle change in the SPR measurement and designates a minimum value in the optimal resonance condition. A movement amount of the angle is corresponding to a movement amount of the SPR angle, and a change in a value of ψ can be also used for calculating the resonance angle. The Δ which designates the phase change can be used in performing precise SPR measurement, and the phase change is maximal under the optimal SPR condition (referring to FIGS. 6 and 7). Therefore, if the change in a phase value in the optimal SPR condition is measured, it can be used in adsorption dynamic property of various bio materials (e.g., adsorption dynamic property of a low molecular material used as a new drug candidate, etc.), which requires a precise measurement, and it can be also used in calculation and quantifying of the SPR angle by simultaneously using the amplitude and the phase.

In the processing method in the sensor of FIG. 4, an ellipsometric coefficient ψ, Δ is calculated from the principle of the ellipsometry having a polarizer-sample-analyzer (PSA) or polarizer-sample-compensator-analyzer (PSCA) type structure in each unit device (the unit pixel in case of CCD).

In the ellipsometric equation, a complex reflection coefficient ratio ρ is a reflection coefficient ratio (r$_s$, r$_p$) with respect to p-wave and s-wave, and can be expressed as follows.

$$\rho = \frac{r_p}{r_s} = \tan\Psi e^{i\Delta}$$

In addition, it is preferable to further provide a collimator 100 which is disposed between the light source 10 and the polarizer 20 so as to convert the light emitted from the light source 10 into parallel light and then transmit the parallel light to the polarizer 20.

Further, it is preferable to further provide a compensator 80 which is disposed between the beam splitter 30 and the SPR sensing part 40 or between the beam splitter 30 and the optical detector 60 so as to compensate the light split from the beam splitter 30.

As shown in FIG. 4, there may be further provided a slit as well as a rotating means or a polarization-modulating means (not shown) for rotating the second polarizer 51 in a vertical direction to a running direction of the light, so that the light polarized by the second polarizer 51 can be independently detected at each incident angle by the optical detector 70 so as to grasp a wavelength property. In the same way, there may be further provided a rotating means (not shown) for rotating the compensator 80 in the vertical direction to the running direction of the light, so that the light compensated by the compensator 80 can be independently detected at each incident angle by the polarized light detecting part 50.

The optimal SPR condition easily changes the wavelength and the angle of the light according to a thickness of the metal thin film 42 deposited on the glass substrate. Therefore, in case that an ellipsometric structure in which the polarizer or the compensator is rotated is used, it is possible to perform the measurement in the optimal SPR condition without deterioration of the sensitivity, which may be occurred by the error of a thickness or physical property when manufacturing the metal thin film 42.

In a method of simultaneously measuring the wavelength and the angle using the ellipsometric structure in which the polarizer or the compensator is rotated, it is possible to perform the measurement in real-time under the optimal SPR condition that can be changed according to a process condition. The phase measurement using the ellipsometry is most sensitively changed in the optimal SPR condition. However, since the refractive index and the thickness of the metal thin film 42 that is a core part of the SPR sensor may be easily changed according to a manufacturing process, it is possible to easily obtain the optimal SPR condition within a measuring angle and a wavelength range and thus it is possible to simultaneously use the advantage of the SPR and the ellipsometry.

A reference numeral 100 which is not descried is an interference filter.

Embodiment

1. Measurement of Angle and Wavelength that Generates SPR

Figure 5:
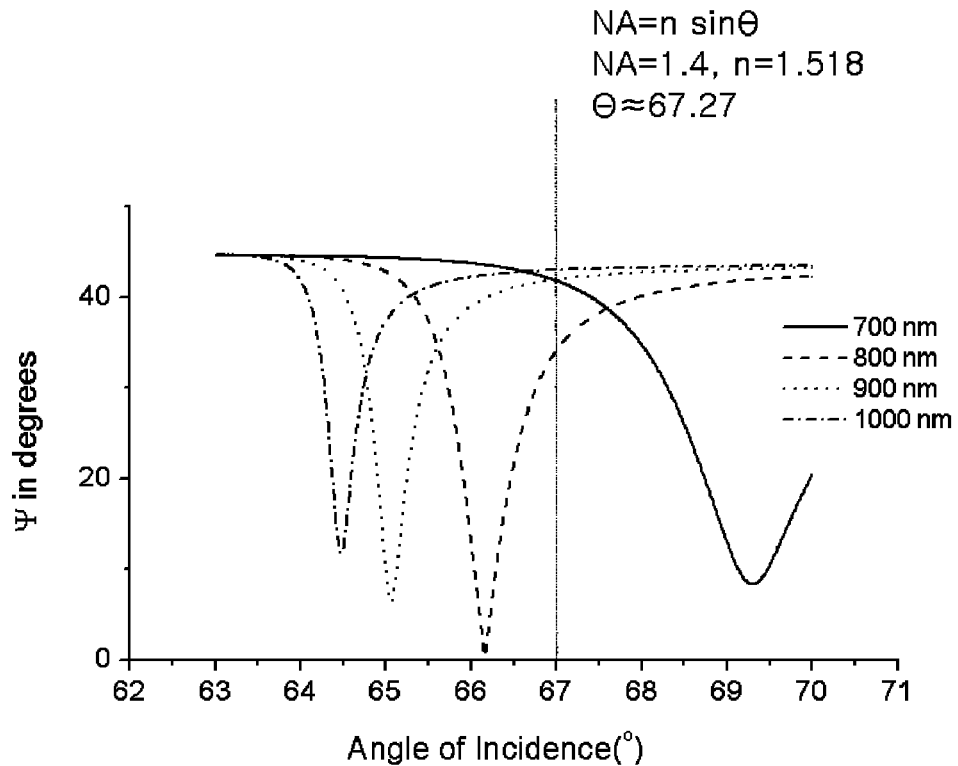
FIG. 5 is a graph showing a SPR condition according to a wavelength when using BK7 lens.

The angle and the wavelength that generates the SPR was measured and then shown in FIG. 5, wherein the wavelength was 750 to 1100 nm, the glass substrate 45 was formed of BK7, the metal thin film was formed of Au, a thickness of the metal thin film was 45 nm, and a refractive index of the buffer solution was 1,333.

As shown in the drawing, if the refractive indexes of the lens and the glass substrate are further increased, the SPR can be generated in a smaller angle and shorter wavelength region.

2. Measurement of Change in Reflexibility and Ellipsometric Coefficient According to Angle The reflexibility and the ellipsometric coefficient according to the angle was measured and then shown in FIGS. 6 and 7, wherein the wavelength was 850, the glass substrate 45 was formed of SF10, the metal thin film was formed of Au, a thickness of the metal thin film was 45 nm, a thickness of the bio thin film is 0 nm and 1 nm (n=1.45), and a refractive index of the buffer solution was 1,333.

Figure 6:
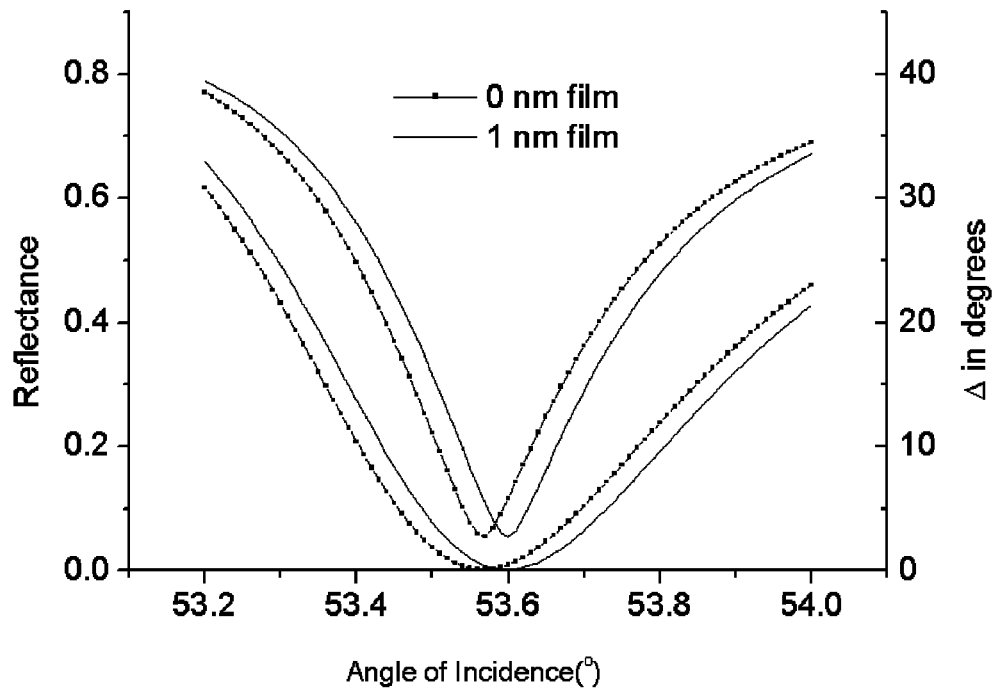
FIG. 6 is a graph showing a change in reflexibility according to an angle change, when a metal thin film having a thickness of 45 nm is coated on SF10 glass and a wavelength is 860 nm.
Figure 7:
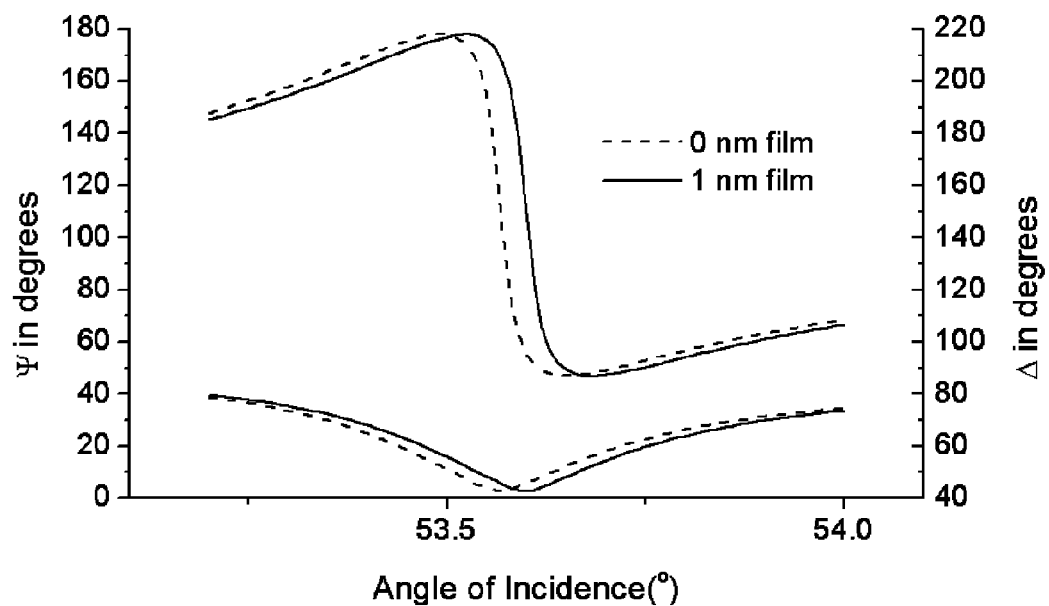
FIG. 7 is a graph showing a change in ellipsometric coefficient according to an angle change, when a metal thin film having a thickness of 45 nm is coated on SF10 glass and a wavelength is 860 nm.

As shown in FIG. 6, the ellipsometric coefficient relevant to the amplitude provides information like the SPR angle change, and as shown in FIG. 7, the phase change is sensitively changed in the optimal SPR condition. By using the sensitive change, it is possible to perform the high sensitive measurement of the surface conjugation property of the bio material in real-time. Particularly, when a low molecular material used as a new drug candidate is conjugated to target protein, it is required to provide the extremely sensitive measurement precision. In this case, it is possible to perform the measurement having higher sensitivity than a conventional SPR measuring method only using the reflexibility.

3. Measurement of Change in SPR Angle According to Wavelength

Figure 8:
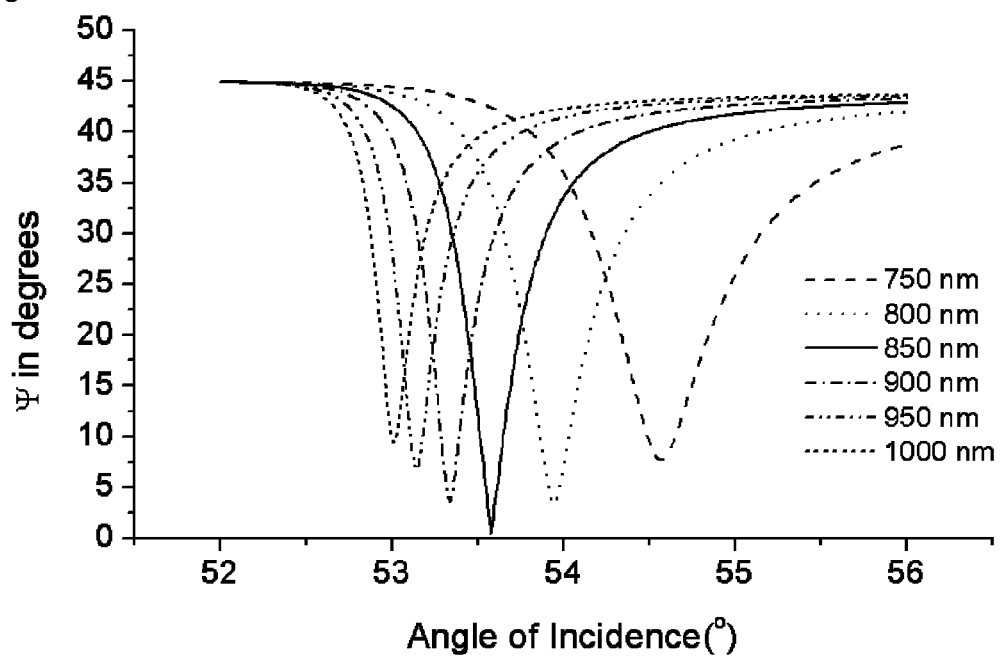
FIG. 8 is a graph showing a change in SPR angle according to a wavelength.
Figure 9:
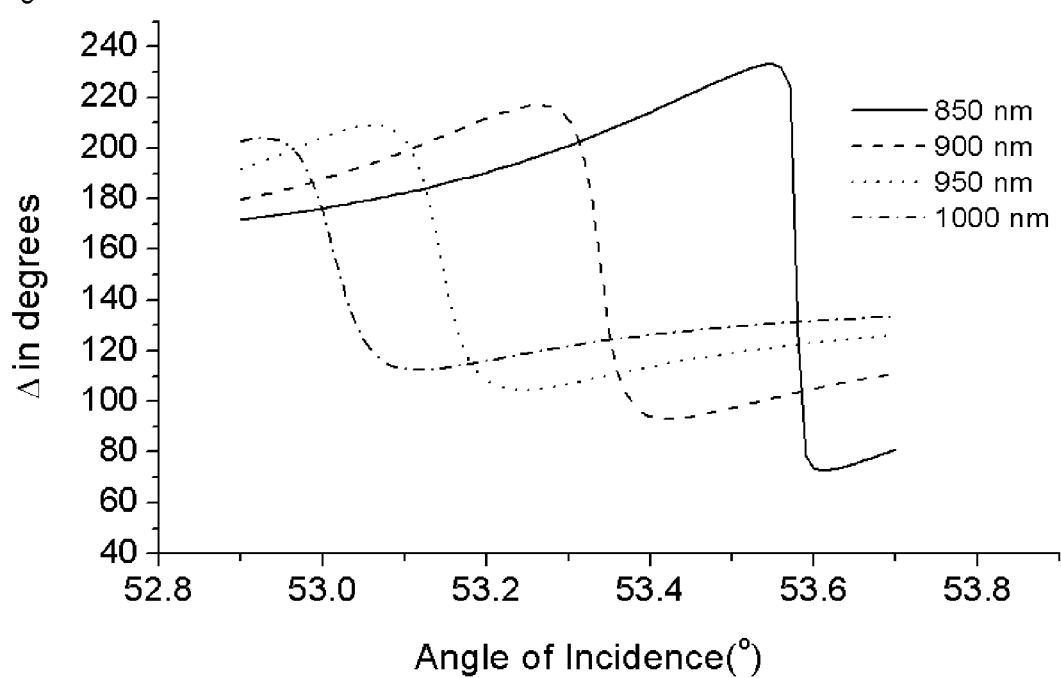
FIG. 9 is a graph showing an inclination of a phase change according to a wavelength and an angle.

The change in the SPR angle according to the wavelength was measured and then shown in FIGS. 8 and 9, wherein the wavelength was 750 to 1000 nm, the lens was formed of SF10, the metal thin film was formed of Au, a thickness of the metal thin film was 44 nm, and a refractive index of the buffer solution was 1,333.

FIG. 8 shows that the SPR angle is changed according to the wavelength, and FIG. 9 shows that an inclination of the phase change is changed according to the angle and the wavelength and also it is possible to select the angle and the wavelength in which the inclination of the phase change becomes maximal.

The invention claimed is:

1. A surface plasmon resonance sensor comprising:
   a vertical illuminating focused-beam ellipsometer, in which light is polarized, a part of the polarized light is focused to a metal thin film by using a surface plasmon resonance (SPR) sensing part, and then the polarized light reflected from the metal thin film is detected;
   the surface plasmon resonance (SPR) sensing part provide to generate SPR according to an angle change of the polarized light, the SPR sensing part including: a first lens which is a converging lens for focusing a part of the polarized light; and a second lens which is formed of a spherical lens or an aspherical lens, or a combination of a spherical lens and an aspherical lens so as to have the metal thin film deposited at a lower side thereof; and
   a flow unit which supplies a buffer solution containing a bio material binding to or dissociation from the metal thin film generating surface plasmon,
   wherein the SPR by change in an angle and a wavelength and the ellipsometric phase change are simultaneously detected by an optical detector.

2. The surface plasmon resonance sensor of claim 1, wherein the vertical illuminating focused-beam ellipsometer comprises a light source; a polarizer for polarizing light emitted from the light source; a beam splitter for splitting the light polarized from the polarizer; an analyzing means for polarizing the light reflected from the metal thin film and passed through the beam splitter; the optical detector detecting amplitude and phase of the light; and a processing device for processing the ellipsometric phase change detected by the optical detector,
   wherein a part of the polarized light split from the beam splitter is focused on the metal thin film further comprising multiple channels.

3. The surface plasmon resonance sensor of claim 2, wherein the light source is one of a light source for emitting a wavelength or a wavelength band of an ultraviolet ray, visible ray or an infrared ray, and a wavelength variable light source of a wavelength variable laser or diode.

4. The surface plasmon resonance sensor of claim 2, wherein the analyzing means comprises:
   a second polarizer for polarizing the light reflected from the metal thin film and passed through the SPR sensing part and the beam splitter;
   a slit for passing the light polarized by the second polarizer; and
   a monochromator for detecting the polarized light passing through slit.

5. The surface plasmon resonance sensor of claim 4, further comprising a rotator or a photoelastic modulator that rotates the polarizer or the second polarizer.

6. The surface plasmon resonance sensor of claim 4, further comprising a rotator that rotates the second polarizer in a vertical direction to a propagation direction of the light, so that the light polarized by the second polarizer can be independently detected at each incident angle by the monochromator.

7. The surface plasmon resonance sensor of claim 2, further comprising a compensator which is disposed between the beam splitter and the SPR sensing part or between the beam splitter and the optical detector so as to compensate the light split from the beam splitter.

8. The surface plasmon resonance sensor of claim 7, further comprising a rotator that rotates the compensator in a vertical direction to a propagation direction of the light, so that the light compensated by the compensator can be detected at each incident angle by the polarized light detecting part.

9. The surface plasmon resonance sensor of claim 2, further comprising a collimator which is disposed between the light source and the polarizer so as to convert the light emitted from the light source into parallel light and then transmit the parallel light to the polarizer.

10. The surface plasmon resonance sensor of claim 1, wherein the converging lens has one of a biconvex shape, a planoconvex shape or a meniscus shape.

* * * * *